United States Patent [19]
Suzuki et al.

[11] Patent Number: 5,565,460
[45] Date of Patent: Oct. 15, 1996

[54] THERAPEUTIC PURINE AGENTS FOR PARKINSON'S DISEASE

[75] Inventors: Fumio Suzuki, Mishima, Japan; Junichi Shimada, Belmont, Mass.; Nobuaki Koike, Sunto-gun, Japan; Shunji Ichikawa, Tagata-gun, Japan; Joji Nakamura, Sunto-gun, Japan; Tomoyuki Kanda, Ealing, United Kingdom; Shigeto Kitamura, Machida, Japan

[73] Assignee: Kyowa Hakko Koygo Co., Ltd., Tokyo, Japan

[21] Appl. No.: 367,346
[22] PCT Filed: Jul. 20, 1994
[86] PCT No.: PCT/JP94/01196
§ 371 Date: Mar. 3, 1995
§ 102(e) Date: Mar. 3, 1995
[87] PCT Pub. No.: WO95/03806
PCT Pub. Date: Feb. 9, 1995

[30] Foreign Application Priority Data

Jul. 27, 1993 [JP] Japan .................. 5-184295

[51] Int. Cl.$^6$ ............... A61K 31/505; A61K 31/54; A61K 31/535; A61K 31/53
[52] U.S. Cl. .................. 514/259; 514/228.2; 514/231.2; 514/245; 514/269; 514/261; 514/359; 514/369; 514/396; 514/406; 514/408; 514/418; 514/430; 514/432; 514/461; 514/468; 514/756
[58] Field of Search .................... 514/242, 244, 514/246, 259, 468, 231.2, 245

[56] References Cited

U.S. PATENT DOCUMENTS 4,831,013   5/1989   Francis ........................ 514/23
5,356,894   10/1994  Rodney et al. ............... 514/233.2

FOREIGN PATENT DOCUMENTS 181282   5/1986   European Pat. Off. .
217748   4/1987   European Pat. Off. .
515107   11/1992  European Pat. Off. .

OTHER PUBLICATIONS

Francis, J. E. "Structure–Activity Profile of a Series of Novel Triazoloquinazoline Adenosine Antagonists", J. Med. Chem. 31: 1014–1020, 1988.

*Primary Examiner*—Theodore J. Criares
*Attorney, Agent, or Firm*—White & Case

[57] ABSTRACT

The present invention relates to a therapeutic agent for Parkinson's disease containing as an active ingredient a polycyclic compound or a pharmaceutically acceptable salt thereof, the compound being represented by the following Formula (I):

and A represents N or $CR^5$ (in which $R^5$ represents hydrogen, or substituted or unsubstituted lower alkyl), or represented by the following Formula (II):

wherein Y, $R^6$ and $R^8$ are as defined herein and B and the adjacent two carbon atoms are combined to form a substituted or unsubstituted, partially saturated or unsaturated, monocyclic or bicyclic, carbocyclic or heterocyclic group.

1 Claim, No Drawings

THERAPEUTIC PURINE AGENTS FOR PARKINSON'S DISEASE

This application is filed under 35 USC 371 of PCT/JP94101196 filed Jul. 20, 1994 which claims parity of Japan application 184,295 filed Jul. 27, 1983.

TECHNICAL FIELD

The present invention relates to a therapeutic agent for Parkinson's disease.

BACKGROUND ART

In connection with Compounds (I) (described afterward) in the present invention, it is known that compounds represented by the following formula

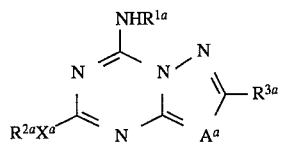

in which $R^{1a}$ represents hydrogen, substituted or unsubstituted lower alkyl, or lower alkanoyl, $R^{2a}$ represents hydrogen, lower alkenyl, substituted or unsubstituted cycloalkyl, substituted or unsubstituted phenyl, substituted or unsubstituted aralkyl, or a substituted or unsubstituted heterocyclic group, $R^{3a}$ represents a substituted or unsubstituted 5-membered heterocyclic group, $X^a$ represents O, S, S(O), S(O)$_2$, or NR$^{4a}$ (in, which R$^{4a}$ represents hydrogen, or substituted or unsubstituted lower alkyl, or R$^{2a}$ and NR$^{4a}$ are combined to form a substituted or unsubstituted 4 to 6-membered saturated heterocyclic group), and $A^a$ represents N or CR$^{5a}$ (in which R$^{5a}$ represents hydrogen, or substituted or unsubstituted lower alkyl), and compounds represented by the following formula

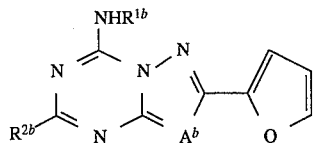

in which $R^{1b}$ represents hydrogen, substituted or unsubstituted lower alkyl, or lower alkanoyl, $R^{2b}$ represents substituted or unsubstituted lower alkyl, lower alkenyl, lower alkynyl, substituted or unsubstituted phenyl, or a substituted or unsubstituted 5- or 6-membered heterocyclic group, and $A^b$ represents N or CR$^{5b}$ (in which R$^{5b}$ represents hydrogen, or substituted or unsubstituted lower alkyl), have an selective adenosine $A_2$ antagonistic activity (Japanese Published Unexamined Patent Application No. 97855.93 and EP 515107A).

Further, in connection with Compounds (II) (described afterward), it is known that compounds represented by the following formula

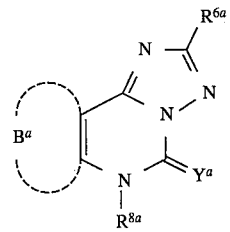

in which $R^{6a}$ represents substituted or unsubstituted phenyl, or a substituted or unsubstituted heterocyclic group, $Y^a$ represents O, S, or NR$^{7a}$ (in which R$^{7a}$ represents hydrogen, substituted or unsubstituted lower alkyl, lower alkenyl, lower alkynyl, substituted or unsubstituted cycloalkyl, or substituted or unsubstituted aryl), $R^{8a}$ represents hydrogen, substituted or unsubstituted lower alkyl, lower alkenyl, substituted or unsubstituted aryl, or substituted or unsubstituted aralkyl, and $B^a$ and the adjacent two carbon atoms are combined to form a substituted or unsubstituted, saturated or unsaturated, monocyclic or bicyclic, carbocyclic or heterocyclic group, have an adenosine $A_2$ antagonistic activity and exhibits an antispasmic activity and a bronchodilating activity [Japanese Published Unexamined Patent Application Nos. 165386/86 and 135475/87, J. Med. Chem., 31, 1014 (1988)].

DISCLOSURE OF THE INVENTION

The present invention relates to a therapeutic agent for Parkinson's disease containing as an active ingredient a polycyclic compound, or a pharmaceutically acceptable salt thereof, the compound being represented by the following Formula (I):

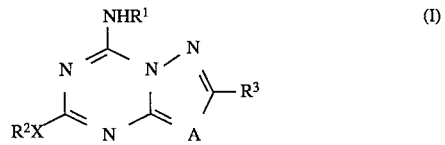

in which, $R^1$ represents hydrogen substituted or unsubstituted lower alkyl, or substituted or unsubstituted lower alkanoyl; $R^2$ represents hydrogen, substituted or unsubstituted lower alkyl, substituted or unsubstituted lower alkenyl, substituted or unsubstituted cycloalkyl, substituted or unsubstituted aryl, substituted or unsubstituted aralkyl, or a substituted or unsubstituted heterocyclic group; $R^3$ represents a substituted or unsubstituted heterocyclic group; X represents a single bond, O, S, S(O), S(O)$_2$, or NR$^4$ (in which R$^4$ represents hydrogen, or substituted or unsubstituted lower alkyl; or R$^2$ and NR$^4$ are combined to form a substituted or unsubstituted 4 to 6-membered saturated heterocyclic group); and A represents N or CR$^5$ (in which R$^5$ represents hydrogen, or substituted or unsubstituted lower alkyl), or represented by the following Formula (II):

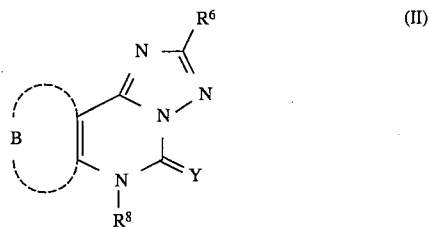

in which $R^6$ represents substituted or unsubstituted aryl, or a substituted or unsubstituted heterocyclic group; Y represents O, S, or NR$^7$ (in which R$^7$ represents hydrogen, substituted or unsubstituted lower alkyl, substituted or unsubstituted cycloalkyl, or substituted or unsubstituted aryl); R$^8$ represents hydrogen, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, or a substituted or unsubstituted heterocyclic group; and B and the adjacent two carbon atoms are combined to form a substituted or unsubstituted, partially saturated or unsaturated, monocyclic or bicyclic, carbocyclic or heterocyclic group.

The compounds represented by Formula (I) and Formula (II) are hereinafter referred to as Compound (I) and Compound (II), respectively, and the same applies to the compounds of other formula numbers.

In the definitions of the groups in Formula (I) and Formula (II), the lower alkyl means a straight-chain or branched alkyl group having 1 to 6 carbon atoms such as methyl, ethyl, propyl, isopropyl, butyl, isobutyl, sec-butyl, tert-butyl, pentyl, neopentyl, and hexyl. The lower alkanoyl means a straight-chain or branched alkanoyl group having 1 to 7 carbon atoms such as formyl, acetyl, propionyl, butyryl, isobutyryl, pivaloyl, and hexanoyl. The lower alkenyl means a straight-chain or branched alkenyl group having 2 to 6 carbon atoms such as vinyl, 1-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, and 5-hexenyl. The lower alkynyl means a straight-chain or branched alkynyl group having 2 to 4 carbon atoms such as ethynyl, 1-propynyl, 2-propynyl, 1-butynyl, and 2-butynyl. The cycloalkyl means a cycloalkyl group having 3 to 8 carbon atoms such as cyclopropyl, cyclobutyl, cyclopentyl, cyclohexyl, cycloheptyl, and cyclooctyl, a bicycloalkyl group having 7 to 12 carbon atoms such as norbornyl, or a tricycloalkyl group having 7 to 12 carbon atoms. Examples of the aryl are phenyl, naphthyl, indenyl, and anthryl. The aralkyl means an aralkyl group having 7 to 15 carbon atoms such as benzyl, 1-phenylethyl, 2-phenylethyl, 2-phenylpropyl, and diphenylmethyl. Examples of the heterocyclic group are furyl, thienyl, pyrrolyl, pyranyl, thiopyranyl, pyridyl, oxazolyl, thiazolyl, imidazolyl, pyrimidyl, triazinyl, indolyl, quinolyl, purinyl, benzoxazolyl, benzothiazolyl, and benzimidazolyl. Examples of the 4 to 6-membered saturated heterocyclic group are azetidino, pyrrolidino, morpholino, and thiomorpholino. Examples of the partially saturated or unsaturated, monocyclic or bicyclic carbocyclic group are cyclopentene, cyclohexene, cycloheptene, and 1,4-dihydronaphthalene. Examples of the partially saturated or unsaturated, monocyclic or bicyclic heterocyclic group are piperidein, tetrahydrobenzo[b]thiophene, isoxazole, oxazole, thiazole, pyrazole, furan, thiophene, pyrrole, pyran, thiopyran, dithine, pyrimidine, imidazole, and benzimidazole.

The substituted lower alkyl, the substituted lower alkanoyl, the substituted lower alkenyl, the substituted lower alkynyl, the substituted cycloalkyl, the substituted aryl, the substituted aralkyl, the substituted heterocyclic group, the substituted 4 to 6-membered saturated heterocyclic group, and the substituted partially saturated or unsaturated, monocyclic or bicyclic, carbocyclic or heterocyclic group each has 1 to 3 independently-selected substituents. Examples of the substituents are lower alkyl, hydroxy, hydroxy-lower alkyl, halogeno-lower alkyl, lower alkoxy, lower alkoxycarbonyl, lower alkylthio, lower alkylsulfinyl, lower alkylsulfonyl, aryloxy, aralkyloxy, halogeno-aryloxy, halogeno-aralkyloxy, carboxy, carbamoyl, lower alkanoyl, aroyl, aryl, halogen, nitro, amino, cyano, trifluoromethyl, and substituted or unsubstituted aralkyl. The lower alkyl and the lower alkyl moiety of the hydroxy lower alkyl, halogeno-lower alkyl, the lower alkoxy, the lower alkoxycarbonyl, the lower alkylthio, the lower alkylsulfinyl, and the lower alkylsulfonyl have the same meaning as the lower alkyl defined above. The aryl and the aryl moiety of the aryloxy, halogeno-aryloxy, and the aroyl have the same meaning as the aryl defined above. The aralkyl and the aralkyl moiety of the aralkyloxy and halogeno-aralkyloxy have the same meaning as the aralkyl defined above. The lower alkanoyl has the same meaning as the lower alkanoyl defined above. The halogen and the halogen moiety of the halogeno-lower alkyl, the halogeno-aryloxy, and the halogeno-aralkyloxy include fluorine, chlorine, bromine, and iodine. Examples of the substituents of the substituted aralkyl are lower alkyl, hydroxy, and halogen, and the lower alkyl and the halogen have the same meanings as the lower alkyl defined above and the halogen defined above, respectively.

The above-mentioned pharmaceutically acceptable salts of Compounds (I) and Compounds (II) include pharmaceutically acceptable acid addition salts, metal salts, ammonium salts, organic amine addition salts, and amino acid addition salts.

Examples of the pharmaceutically acceptable acid addition salts of Compounds (I) and Compounds (II) are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

Compounds (I) and Compounds (II) including novel compounds can be produced according to the methods disclosed in the above-described literatures or similar methods thereto. The desired compounds in the processes can be isolated and purified by purification methods conventionally used in organic synthetic chemistry, for example, filtration, extractions, washing, drying, concentration, recrystallization, and various kinds of chromatography.

In the case where a salt of Compound (I) or Compound (II) is desired and it is produced in the form of the desired salt, it can be subjected to purification as such. In the case where Compound (I) or Compound (II) is produced in the free state and its salt is desired, Compound (I) or Compound (II) is dissolved or suspended in a suitable solvent, followed by addition of an acid or a base to form a salt.

Compounds (I), Compounds (II), and pharmaceutically acceptable salts thereof may be in the form of adducts with water or various solvents, which can also be used as the therapeutic agents of the present invention.

Some of Compounds (I) and Compounds (II) can exist in the form of optical isomers, and all possible stereoisomers including the above-mentioned ones and mixtures thereof can also be used as the therapeutic agents of the present invention. With regard to Compounds (II), isomers represented by Formula (IIb), Formula (IIc), and Formula (IId) illustrated below can exist, and all these isomers can also be used as the therapeutic agents of the present invention.

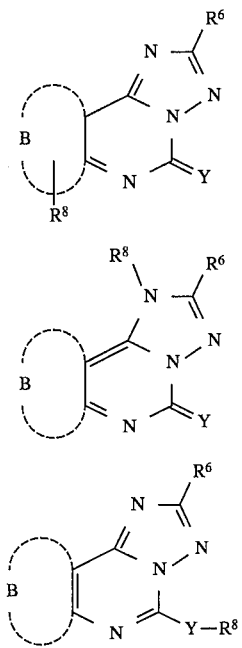

(In the formulae, $R^6$, $R^8$, Y, and B have the same meanings as defined above.)

Examples of Compound (I) and Compound (II) are shown in Table 1.

TABLE 1

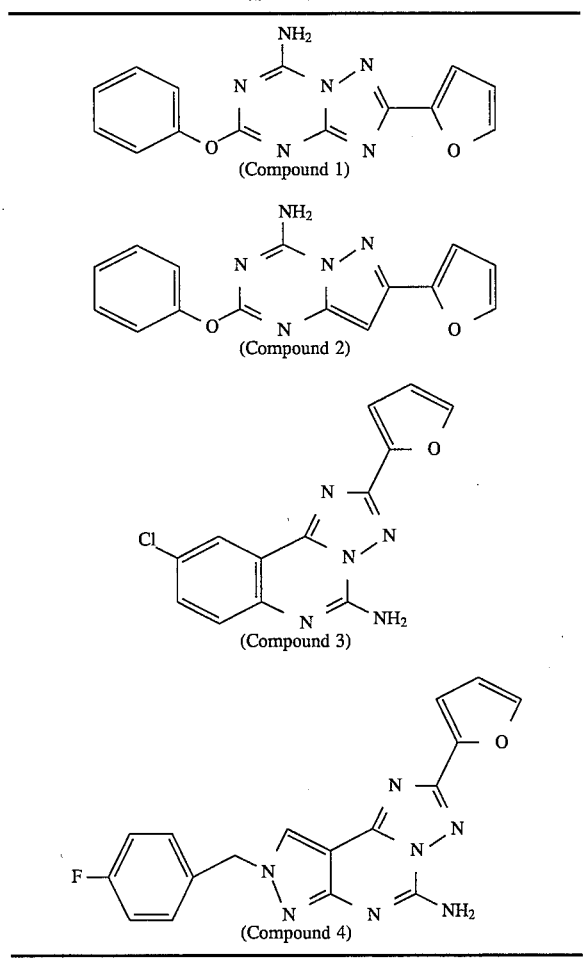

Compound 1: 7-Amino-2-(2-furyl)-5-phenoxy [1,2,4]triazolo[1,5-a]-1,3,5-triazine (compound disclosed in Example 1 of Japanese Published Unexamined Patent Application No. 97855/93)

Melting Point: 250.7°–251.7° C.

Elemental Analysis: $C_{14}H_{10}N_6O_2$

Calcd. (%): C, 57.14; H, 3.43; N, 28.56

Found (%): C, 56.89; H, 3.36; N, 28.35

NMR (DMSO-$d_6$) δ (ppm): 9.00(2H, brs), 7.92 (1H, J=1.5 Hz), 7.49–7.43 (2H, m), 7.28–7.23 (3H, m), 7.12 (1H, d, J=3.0 Hz), 6.70(1H, dd, J=1.5, 3.0 Hz)

Compound 2: 7-Amino-2-(2-furyl)-5-phenoxypyrazolo[2,3-a]-1,3,5-triazine (compound disclosed in Example 119 of Japanese Published Unexamined Patent Application No. 97855/93)

Melting Point: 274.1°–b 276.2° C.

Elemental Analysis: $C_{15}H_{11}N_5O_2 \cdot \frac{1}{4}H_2O$

Calcd. (%): C, 60.50; H, 3.89; N, 23.52

Found (%): C, 60.69; H, 3.54; N, 23.61

IR (KBr) $\nu_{max}$ (cm$^{-1}$): 1664, 1603, 1552

NMR (DMSO-$d_6$) δ (ppm): 8.82(1H, brs), 8.46(1H, brs), 7.84 (1H, d, J=1.0 Hz), 7.47–7.41(2H, m), 7.28–7.21 (3H, m), 7.00(1H, d, J=3.0 Hz), 6.66(1H, dd, J=1.0, 3.0 Hz), 6.43 (1H, s)

Compound 3: 5-Amino-9-chloro-2-(2-furyl)-1,2,4-triazolo-[1,5-c]quinazoline (compound disclosed in Example 33 of Japanese Published Unexamined Patent Application No. 165386/86)

Melting Point: 257°–259° C.

Elemental Analysis: $C_{13}H_8CN_5O \cdot 0.4(CH_3)_2NCHO$

Calcd. (%): C, 54.16; H, 3.46; N, 24.02

Found (%): C, 53.90; H, 3.31; N, 24.09

IR (KBr) $\nu_{max}$ (cm$^{-1}$): 1682, 1614, 1589, 1555, 1528, 1480,

NMR (DMSO-$d_6$) δ (ppm): 8.17(1H, d, J=2.5 Hz), 8.02(2H, brs), 7.99–7.98 (1H, m), 7.71 (1H, dd, J=2.5, 8.7 Hz), 7.57(1H, d, J=8.7 Hz), 7.28(1H, d, J=3.5 Hz), 6.76(1H, dd, J=2.5, 3.5 Hz)

$^{13}$C NMR (DMSO-$d_6$) δ (ppm): 155.6, 150.8, 145.2, 144.9, 143.7, 132.2, 126.9, 126.8, 122.1, 114.1, 112.3, 112.1

Compound 4: 5-Amino-8-(4-fluorobenzyl)-2-(2-furyl)pyrazolo-[4,3-e]-1,2,4-triazolo[1,5-c]pyrimidine [compound 18f disclosed in Eur. J. Med. Chem., 28, 569 (1993)]

Melting Point: 276.1°–277.8° C.

FAB-MS (M/Z): 350 (M$^+$+H)

IR (KBr) $\nu_{max}$ (cm$^{-1}$): 1689, 1680, 1621, 1528, 1515, 1225

NMR (DMSO-$d_6$) δ (ppm): 8.75 (1H, s), 7.94 (1H, d, J=0.7 Hz), 7.64 (2H, s), 7.43–7.38 (2H, m), 7.23–7.16 (3H, m), 6.74–6.73(1H, m), 5.49(2H, s)

The pharmacological activities of Compound (I) and Compound (II) are shown below by experimental examples.

Experimental Example 1 Effect on Locomotor Activity in Parkinson's Disease Model in Mice 1-Methyl-4-phenyl-1,2,3,6-tetrahydropyridine (MPTP) causes symptoms of Parkinson's disease in humans Science, 219, 979 (1983)]. It is reported that an experimental Parkinson's disease model was obtained by administering MPTP to mice [Science, 224, 1451 (1984)]. If a compound is effective on the experimental Parkinson's disease model in mouse, the compound can be expected to have a therapeutic effect on Parkinson's disease.

The experiment was performed by using several groups of 7-weeks-old male C57BL/6 mice (weighing 20 to 24 g, Japan SLC), each group consisting of 8 mice. MPTP (RBI Co., Ltd. ) dissolved in a physiological saline solution (Otsuka Pharmaceutical Co., Ltd. ) was intraperitoneally administered to each mouse once a day for five consecutive days at a dose of 30 mg/kg. Test compounds were suspended in injectable distilled water (Otsuka Pharmaceutical Co., Ltd.) containing Tween 80 [polyoxyethylene (20) sorbitan monooleate]. L-DOPA (Kyowa Hakko Kogyo Co., Ltd. ) was suspended in 0.3% CMC (sodium carboxymethylcellulose). Thirty minutes after the final MPTP administration, the test compound suspensions and the control suspension [injectable distilled water (Otsuka Pharmaceutical Co., Ltd.) containing Tween 80] containing no test compound were orally administered to separate groups of the mice (0.1 ml per 10 g of body weight). The amount of active movements of each mouse was measured by using Automex-II (Columbus Instruments International Corp.) for the period of 30 minutes starting 30 minutes after the administration of the test compound. The effect of the compounds was evaluated by comparing the average counts of the active movements of the test compound-administered groups with those of the control groups. Statistical comparison of the values was carried out by Williams-Wilcoxon test.

The results are shown in Table 2.

TABLE 2

| Group | Administration | | Dose of Test Compound (mg/kg) | Amount of Active Movements (average count ± S.E.M) |
|---|---|---|---|---|
| Normal | MPTP | (−) | | |
| Control | Test Compound | (−) | — | 1984 ± 122.3 |
| MPTP | MPTP | (+) | | |
| | Test Compound | (−) | — | 41 ± 14.3## |
| Compound | MPTP | (+) | | |
| | Compound 1 | (+) | 10 | 785 ± 87.3** |
| Normal | MPTP | (−) | | |
| Control | Test Compound | (−) | — | 1875 ± 77.7 |
| MPTP | MPTP | (+) | | |
| | Test Compound | (−) | — | 207 ± 85.5## |
| L-DOPA | MPTP | (+) | | |
| | L-DOPA | (+) | 300 | 561 ± 271.01[1)] |

$p<0.01$ (comparison with normal control group)
**$p<0.01$ (comparison with MPTP-treated group)
[1)]no significant difference as compared with MPTP-treated group)

Experimental Example 2 Effect on Haloperidol-Induced Catalepsy

The experiment was performed by using several groups of 5-weeks-old male ddY mice (weighing 22.to 24 g, Japan SLC), each group consisting of 5 mice. Haloperidol (Janssen Pharmaceutical) suspended in 0.3% CMC was intraperitoneally administered to each mouse at a dose of 1.0 mg/kg. Test compounds were suspended in 0.3% CMC or in injectable distilled water (Otsuka Pharmaceutical Co., Ltd.) containing Tween 80. L-DOPA (Kyowa Hakko Kogyo Co., Ltd.) and benserazide hydrochloride (Kyowa Hakko Kogyo Co., Ltd.) were suspended in 0.3% CMC. One hour after the haloperidol administration, the test compound suspensions and the control suspension [injectable distilled water (Otsuka Pharmaceutical Co., Ltd.) containing Tween 80] containing no test compound were orally administered to separate groups of the mice (0.1 ml per 10 g of body weight). One hour after the administration of the test compound, the forelimbs of each mouse and subsequently the hindlimbs of the same mouse were placed on a 4.5 cm-high, 1.0 cm-wide bar and catalepsy was estimated. All of the test compounds were orally administered at a dose of 10 mg/kg, and L-DOPA (100 mg/kg) and benserazide (25 mg/kg) were intraperitoneally administered together as a control experiment. The catalepsy score and the standard of judgment are shown. below.

| score | | duration of the cataleptic posture | |
|---|---|---|---|
| 0: | | forelimbs | less than 5 seconds |
| | | hindlimbs | less than 5 seconds |
| 1: | | forelimbs | from 5 (inclusive) to 10 (exclusive) seconds |
| | | hindlimbs | less than 5 seconds |
| 2: | | forelimbs | 10 seconds or more |
| | | hindlimbs | less than 5 seconds |
| 3: | | forelimbs | from 5 (inclusive) to 10 (exclusive) seconds |
| | | hindlimbs | from 5 (inclusive) to 10 (exclusive) seconds; |
| | or | forelimbs | less than 5 seconds |
| | | hindlimbs | 5 seconds or more |
| 4: | | forelimbs | 10 seconds or more |
| | | hindlimbs | from 5 (inclusive) to 10 (exclusive) seconds; |
| | or | forelimbs | from 5 (inclusive) to 10 (exclusive) seconds |
| | | hindlimbs | 10 seconds or more |
| 5: | | forelimbs | 10 seconds or more |
| | | hindlimbs | 10 seconds or more |

The effect of the compounds was evaluated by the total of the catalepsy scores of five mice in each group (25 points at the full). The groups wherein the total score was not more than 20 point is were estimated to be effective. The number of the animals showing remission against catalepsy is the number of the mice for which the catalepsy score was not more than 4 points. The remission rate shows the rate of decrease in total score based on that of the control group.

The $ED_{50}$ (50% effective dose) values were determined using ten mice at each dose. A test compound was judged to be effective at the dose where the catalepsy score was 3 or less than 3. The $ED_{50}$ values were calculated by Probit analysis.

TABLE 3

| Compound No. | Total Score | Number of the Animals Showing Remission | Remission Rate (%) | $ED_{50}$ (mg/kg) |
|---|---|---|---|---|
| 0.3% Tween 80 (Control) | 25 | 0 | 0 | |
| L-DOPA + benserazide | 18 | 4 | 28 | 107.5 |
| 1 | 5 | 5 | 80 | 1.3 |
| 2 | 17 | 4 | 32 | |
| 3 | 13 | 4 | 48 | |
| 4 | 12 | 3 | 52 | |

Experimental Example 3 Augmentation of the Contralateral

Rotation in Rats with a 6-Hydroxydopamine-Induced

Unilateral Lesion of the Nigrostriatal Dopamine Pathway

When a unilateral lesion of the nigrostriatal pathway is induced by 6-hydroxydopamine in rodents, the sensitivity of dopamine receptors in the denervated striatum is enhanced. Administration of a dopamine against to the rodents in such a condition induces a rotational behavior to the side contralateral to the lesioned side [Acta Physiol. Scand., 367, 69 (1971)]. This model has been used for a long time as a model for the study of Parkinson's disease and in the screening of drugs for this disease [Neurol. Neurobiol.; 33, 1 (1987)].

Male Sprague-Dawley rats (weighing 200 to 240 g, Japan SLC) were pretreated with desipramine hydrochloride (25 mg/kg, i.p., Sigma Co.) 30 minutes before surgery to protect noradrenergic neurons. Then, the animals were: anesthetized with sodium pentobarbital (30 mg/kg, i.p., Dainippon Pharm. Co., Ltd.) and the nigrostriatal pathway was lesioned by injection of 6-hydroxydopamine hydrobromide (8 µg, Sigma Co.) into the left medial forebrain bundle. 6-Hydroxydopamine hydrobromide was dissolved in physiological saline containing 0.05% L-ascorbic acid (Wako Pure Chem. Industries, Ltd.) to make 2 µl. of solution and injected over 3 minutes.

More than 10 days after surgery, each rat was placed in a plastic bowl (30 cm in diameter). Apomorphine (0.1 mg/kg, Sandoz, AG) was injected subcutaneously arid the rats which showed a rotational behavior to the side contralateral to the lesioned side at a frequency of more than 600 counts/60 minutes after apomorphine administration were used for screening. The number of rotations was counted with an automated rotometer, in which each 180° turn was counted as a rotation.

Test compounds were suspended in 0.3% sodium carboxymethylcellulose and administered orally at a dose of 10 mg/kg 30 minutes before the injection of apomorphine (0.1 mg/kg, s.c.). The counts of rotations were summed up every 5 minutes for 150 minutes after apomorphine administration. The total rotation counts induced by apomorphine (0.1 mg/kg, s.c.) with and without a test compound were statistically compared, using the same animals. Rats were allowed to rest more than 5 days between each experiment. Statistical comparison of the values was carried out by Sign-Wilcoxon test.

TABLE 4

| Compd. No. | total rotation counts (average count ± S.E.M.) | |
| --- | --- | --- |
|  | apomorphine | test compound + apomorphine |
| 1 | 706 ± 59 | 1011 ± 139* |

*$p<0.05$

Experimental Example 4 Acute Toxicity Test

Test compounds were orally administered to groups of rid-strain male mice weighing 20±1 g, each group consisting of three mice. Seven days after the administration, minimum lethal dose (MLD) of each compound was determined by observing the mortality.

The MLD values of Compound 1 and Compound 2 are greater than 300 mg/kg, indicating that the toxicity of the compounds is weak. Therefore, these compounds can be safely used in a wide range of doses.

Compound (I), Compound (II), and pharmaceutically acceptable salts thereof exhibit antiparkisonism activity, and are useful as a therapeutic agent for Parkinson's disease.

Compound (I), Compound (II), and pharmaceutically acceptable salts thereof can be administered as they are, or in the form of various pharmaceutical compositions. The pharmaceutical compositions in accordance with the present invention can be prepared by uniformly mixing an effective amount of Compound (I), Compound (II), or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, and the like. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

Injectable preparations can be prepared using a carrier such as distilled water, a salt solution, a glucose solution, or a mixture of a salt solution and a glucose solution. The preparations can be prepared in the form of solution, suspension or dispersion according to a conventional method by using a suitable auxiliary.

Compound (I), Compound (II), and pharmaceutically acceptable salts thereof can be administered orally or parenterally as injections in the said dosage forms. The effective dose and the administration schedule vary depending upon the mode of administration, the age, body weight, and conditions of a patient, etc. However, generally, Compound (I), Compound (II), or a pharmaceutically acceptable salt thereof is administered in a daily dose of 1 to 50 mg/kg in 3 to 4 parts.

Certain embodiments of the invention are illustrated in the following examples.

BEST MODE FOR CARRYING OUT THE INVENTION

EXAMPLE 1 Tablets

Tablets having the following composition were prepared in a conventional manner.

Compound 1 (40 g) was mixed with 286.8 g of lactose and 60 g of potato starch, followed by addition of g of a 10% aqueous solution of hydroxypropylcellulose. The resultant mixture was kneaded, granulated, and then dried by a conventional method. The granules were refined to give granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter.

| Composition of One Tablet | |
|---|---|
| Compound 1 | 20 mg |
| Lactose | 143.4 mg |
| Potato Starch | 30 mg |
| Hydroxypropylcellulose | 6 mg |
| Magnesium Stearate | 0.6 mg |
| | 200 mg |

EXAMPLE 2 Fine Granules

Fine granules having the following composition were prepared in a conventional manner.

Compound 2 (20 g) was mixed with 655 g of lactose and 285 g of corn starch, followed by addition of 400 g of a aqueous solution of hydroxypropylcellulose. The resultant mixture was kneaded, granulated, and then dried by a conventional method to give fine granules containing 20 g of the active ingredient in 1,000 g.

| Composition of One Pack of Fine Granules | |
|---|---|
| Compound 2 | 20 mg |
| Lactose | 655 mg |
| Corn Starch | 285 mg |
| Hydroxypropylcellulose | 40 mg |
| | 1,000 mg |

EXAMPLE 3 Capsules

Capsules having the following composition were prepared in a conventional manner.

Compound 3 (200 g) was mixed with 995 g of Avicel and 5 g of magnesium stearate. The mixture was put in hard capsules No. 4 each having a capacity of 120 mg by using a capsule filler (Model LZ-64, Zanashi) to give capsules; each containing 20 mg of the active ingredient.

| Composition of One Capsule | |
|---|---|
| Compound 3 | 20 mg |
| Avicel | 99.5 mg |
| Magnesium Stearate | 0.5 mg |
| | 120 mg |

EXAMPLE 4 Injections

Injections having the following composition were prepared in a conventional manner.

Compound 4 (1 g) was dissolved in 100 g of purified soybean oil, followed by addition of 12 g of purified egg yolk lecithin and 25 g of glycerine for injection. The resultant mixture was made up to 1,000 ml with distilled water for injection, thoroughly mixed, and emulsified by a conventional method. The resultant dispersion was subjected to aseptic filtration by using 0.2 μm disposable membrane filters, and then aseptically put into glass vials in 2 ml portions to give injections containing 2 mg of the active ingredient per vial.

| Composition of One Injection Vial | |
|---|---|
| Compound 4 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

Industrial Applicability

According to the present invention, there can be provided an excellent therapeutic agent for Parkinson's disease.

We claim:

1. A method of treating Parkinson's disease which comprises administering an effective amount of a polycyclic compound or a pharmaceutically acceptable salt thereof, the compound is of the formula (I):

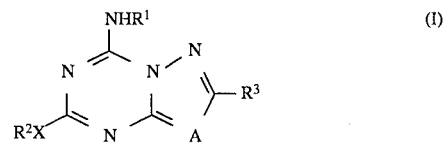

in which, $R^1$ represents hydrogen, substituted or unsubstituted lower alkyl, or substituted or unsubstituted lower alkanoyl; $R^2$ represents hydrogen, substituted or unsubstituted lower alkyl, substituted or substituted lower alkenyl, substituted or unsubstituted cycloalkyl, substituted or unsubstituted aryl, substituted or unsubstituted aralkyl, or a substituted or unsubstituted heterocyclic group; $R^3$ represents a substituted or unsubstituted heterocyclic group; X represents a single bond, O, S, S(O), $S(O)_2$m or $NR^4$, wherein $R^4$ represents hydrogen, or substituted or unsubstituted lower alkyl; or $R^2$ and $NR^4$ are combined to form a substituted or unsubstituted 4 to 6-membered saturated heterocyclic group; and A represents N, $CR^5$ wherein $R^5$ represents hydrogen, or substituted or unsubstituted lower alkyl, or is represented by the formula (II):

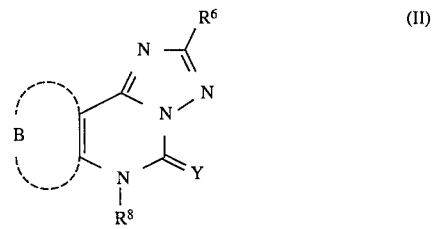

in which $R^6$ represents substituted or unsubstituted aryl, or a substituted or unsubstituted heterocyclic group; Y represents O, S, or $NR^7$ wherein $R^7$ represents hydrogen, substituted or unsubstituted lower alkyl, substituted or unsubstituted cycloalkyl, or substituted or unsubstituted aryl; $R^8$ represents hydrogen, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, or a substituted or unsubstituted heterocyclic group; and B and the adjacent two carbon atoms are combined to form a substituted or unsubstituted, partially saturated or unsaturated, monocyclic or bicyclic, carboncyclic or heterocyclic group.

\* \* \* \* \*

UNITED STATES PATENT AND TRADEMARK OFFICE
CERTIFICATE OF CORRECTION

PATENT NO. : 5,565,460
DATED : October 15, 1996
INVENTOR(S) : Fumio Suzuki et al.

It is certified that error appears in the above-indentified patent and that said Letters Patent is hereby corrected as shown below:

On the title page, item [54] and column 1, line 1, change "PURINE" to --TRIAZINE AND PYRIMIDINE--;

In the cover page, under Assignee, change "Koygo" to --Kogyo--;

Col. 12, line 16, after "administering," insert --to a host in need thereof--;

Col. 12, line 17, delete "'" and after "thereof," insert --wherein--;

Col. 12, line 28, the word after "or" should read --unsubstituted--;

Col. 12, line 33, change "m" to --,--;

Col. 12, line 37, after "N," insert --or--; and

Col. 12, line 62, change "boncyclic" to -- bocyclic--.

Signed and Sealed this

Fifteenth Day of April, 1997

Attest:

BRUCE LEHMAN

*Attesting Officer*     *Commissioner of Patents and Trademarks*